United States Patent
Yang et al.

(10) Patent No.: US 7,866,204 B2
(45) Date of Patent: Jan. 11, 2011

(54) ADAPTIVE REAL-TIME CONTAMINANT DETECTION AND EARLY WARNING FOR DRINKING WATER DISTRIBUTION SYSTEMS

(75) Inventors: Yingping Jeffrey Yang, Cincinnati, OH (US); John Hall, Cincinnati, OH (US); Roy C. Haught, Independence, KY (US); James A. Goodrich, Union, KY (US)

(73) Assignee: The United States of America as represented by the Administrator of the United States Environmental Protection Agency, Washington, DC (US)

( * ) Notice: Subject to any disclaimer, the term of this patent is extended or adjusted under 35 U.S.C. 154(b) by 677 days.

(21) Appl. No.: 11/700,236

(22) Filed: Jan. 31, 2007

(65) Prior Publication Data

US 2008/0178663 A1 Jul. 31, 2008

(51) Int. Cl.
*G01N 15/02* (2006.01)

(52) U.S. Cl. .................................................. 73/61.71
(58) Field of Classification Search ................ 702/188; 73/1.24, 23.33, 61.71
See application file for complete search history.

(56) References Cited

U.S. PATENT DOCUMENTS

| | | | | |
|---|---|---|---|---|
| 6,200,815 | B1 * | 3/2001 | Pasula | 436/63 |
| 7,391,333 | B2 * | 6/2008 | Madden et al. | 340/603 |
| 2002/0148738 | A1 * | 10/2002 | Boyd et al. | 205/782 |
| 2004/0168989 | A1 * | 9/2004 | Tempest, Jr. | 210/760 |
| 2006/0031040 | A1 * | 2/2006 | Wolfe | 702/184 |
| 2006/0277977 | A1 * | 12/2006 | Kahn et al. | 73/53.01 |
| 2007/0219731 | A1 * | 9/2007 | Merwin et al. | 702/55 |

* cited by examiner

*Primary Examiner*—John Fitzgerald

(57) ABSTRACT

A method for monitoring water in a distribution system is disclosed where the sensor sampling schedule is changed in real time in response to a contaminant or other chemical passing through the sampling location. This results in finer determination of where the contaminant is located in the water distribution and identification of the contaminant with a lower false rate than random or scheduled sampling.

9 Claims, 10 Drawing Sheets

ADAPTIVE REAL-TIME CONTAMINANT DETECTION AND EARLY WARNING FOR DRINKING WATER DISTRIBUTION SYSTEMS

I. FIELD OF THE INVENTION

The present invention relates to adaptive techniques and algorithms for real-time contaminant detection at low false rates. It applies to drinking water distribution systems in areas such as early warning systems, homeland security, compliance monitoring and process controls.

II. BACKGROUND OF INVENTION

A distribution system is a network of water pipes, power and storage devices delivering finished water from a water plant to individual users (i.e., residential, commercials, governments, schools and industries). Typically, well or river water is pumped to a water plant for treatment and production. Finished water is then pumped to a water storage tower and flows into a network of pipes toward the end users. Total length for a typical distribution network can be in hundreds of thousand miles. Inside of the pipe flows the water under pressure that can change in geographic locations and vary between time of a day and seasons.

Contaminant detection in a distribution pipe network is the subject of this said invention. Contaminants can be introduced into a distribution system in intentional sabotage, terrorist attack, accident or in naturally occurring incidences such as negative pressure siphoning in broken pipes (AWWA (2004) *Verification and control of pressure transients and intrusion in distribution systems*. AWWA Research Foundation, CO.). In such occasions, contaminated water volume is small compared to water flows inside of the pipe. After entering the pipe, contaminants of a finite volume disperse and transport in the form of a contaminated water body or "slug". At the same time they react with chemical disinfectants that are added to water in compliance of drinking water regulations. A consolidated review of distribution system, disinfectants, and contaminant transport is given in U.S. EPA (2006) Water distribution system analysis: Field studies, modeling and management, a reference guide for utilities. U.S. Environmental Protection Agency, Water Resources and Water Supply Division, Cincinnati, Ohio.

Contaminants in the pipe can cause changes in water quality parameters due to their reactions with the water or even by merely simple mixing. Types of measured parameters that can reflect water quality change include total chlorine, free chlorine, chloride, nitrogen, pH, oxidation-reduction potential (ORP), conductivity, turbidity, and dissolved oxygen (DO). Online water quality sensors are commonly used in measurements. Total organic carbon (TOC) analyzer has been used for detection, but not commonly because of its high capital and operational cost. Furthermore, more advanced compound-specific sensors are under development (U.S. EPA (2005) *Technologies and techniques for early warning systems to monitor and evaluate drinking water quality: A state-of-the-art review. Final Draft*, U.S. Environmental Protection Agency, Office of Water, Washington, D.C., 165p.). At its current form, the said invention relies on conventional water quality sensors.

Two approaches for contaminant detection in water pipes have been proposed. One school uses conventional water quality sensors. Available commercial products such as the Hach Inc. EventMonitor™ fall into this category. Their sophistication varies in contaminant detection, but most identify outliers and anomalies using control chart (e.g., average and standard deviation) or similar statistical techniques. Some products also use comparison of historical variations. Limited to conventional statistical techniques, these commercially available methods and products have high false detection rates some in excess of 30-50%. In collaboration with the U.S. EPA, the Department of Energy (DOE) Sandia National Laboratory (SNL) is incorporating higher levels of statistical methods in anomaly detection. Their methods of multi-variable classification can achieve better results (Klise, et al, (2006) *Water quality change detection: multivariate classification and discrimination algorithms*. In proc. SPIE 06 Defense & Security, Orlando, Fla.), potentially around 10-20%.

Another school of approach is to develop and employ compound specific advanced sensors and instruments. These technologies are based on more advanced detection mechanisms (U.S. EPA, 2005 supra), and capable of providing accurate detection of a target contaminant in drinking water. At this time, no products are available for a wide range of hazardous contaminants in commercial scales. Even when available they are likely to be expensive and require skillful operation and maintenance, a practicality limitation for wide applications.

There is a need to detect contaminants introduced to water pipes and also to measure sudden changes in water quality that can lead to non-compliances of drinking water regulations. One advantage afforded in the present invention is its low false identification rates. The target rate is below 5%. A particular advantage to the present invention is the use conventional water quality sensors rather than advanced sensors, offering advantages in cost and operational logistics

III. SUMMARY OF THE INVENTION

The present invention uses a different technical approach. Instead of relying on conventional statistical classification, it places focus on mathematical and physical representation of a contaminant slug transporting in water pipes. Adaptive detection procedures are employed by using robust statistics of t-series signal variations followed by inter-parameter relationships and spatial correlations. This 3-step adaptive process at its entirety can reduce the false detection rate to less than 5%, preferably less than 1% and more preferably less than 0.1%. This makes contaminant detection and early warning a practical tool in field applications.

The present invention further relates to methods and processes using algorithms created to detect and identify, in real-time, the contamination and water quality changes in a water distribution system.

The basic steps in an adaptive detection procedure embodiment of the invention are: Step one, determining baseline values for water components in the distribution system at a particular local monitoring station. Step two, determining the presence of a contaminant chemical component or an aberrant concentration of a chemical component of the water at that local monitoring station or water plant. Step three, identifying the contaminant chemical or aberrant concentration or determining the location within the water distribution system. Step four, changing the sensor sampling schedule and optionally generating a warning in response to the data from step three.

The present invention is particularly useful for measuring a passing slug of contaminated or altered water as a measure of the presence and location of the contamination in order to isolate and prevent its distribution through the drinking water system.

While the present invention is described in terms of monitoring drinking water in water distribution systems, the same may be applied to any other fluid distribution system with appropriate sensors corresponding to the chemical components and/or likely contaminants for such a fluid system.

III. BRIEF DESCRIPTION OF THE FIGURES

Figure 3:
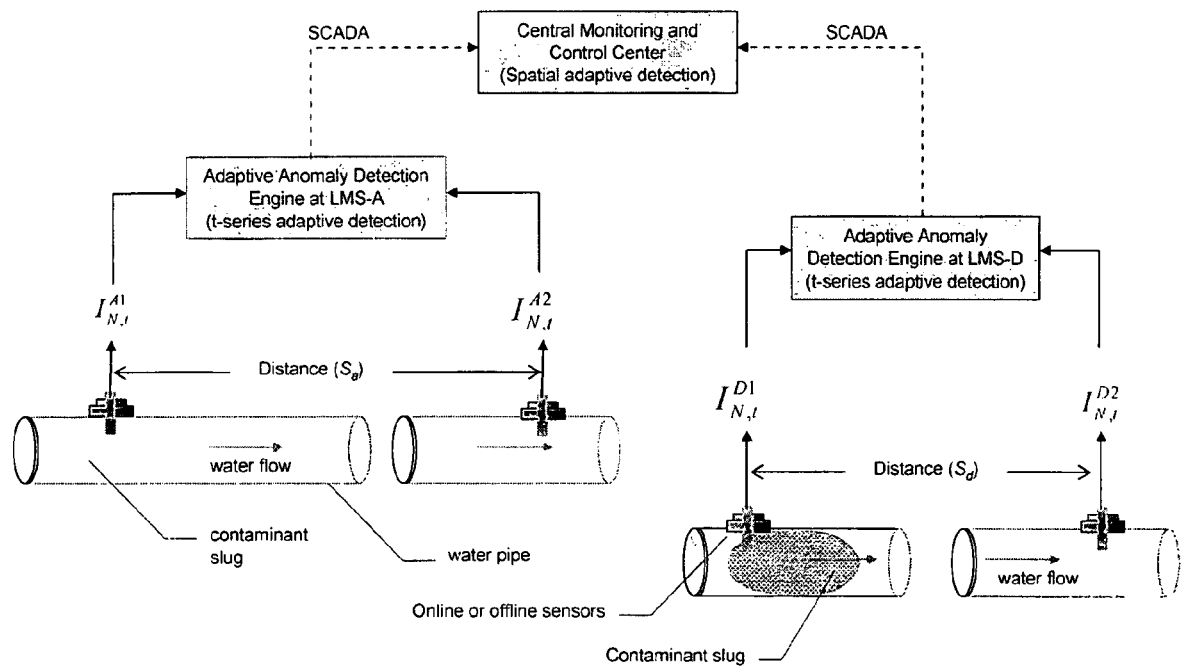

FIG. 3 is a graphic schematic of paired sensors of a local monitoring station (LMS) and their configuration with the central monitoring and control center. A distributed network of paired sensors at local monitoring stations (LMS) and their configuration with the central monitoring and control center is shown. Sensors can be placed either in-pipe or off-stream. Water quality measurements ($I_{t,i}^{A1}, I_{t,i}^{A2}$ or $I_{t,i}^{D1}, I_{t,i}^{D2}$) are transmitted to their specific LMS adaptive detection engines for anomaly detection. LMS A and D are used as examples.

Figure 4:
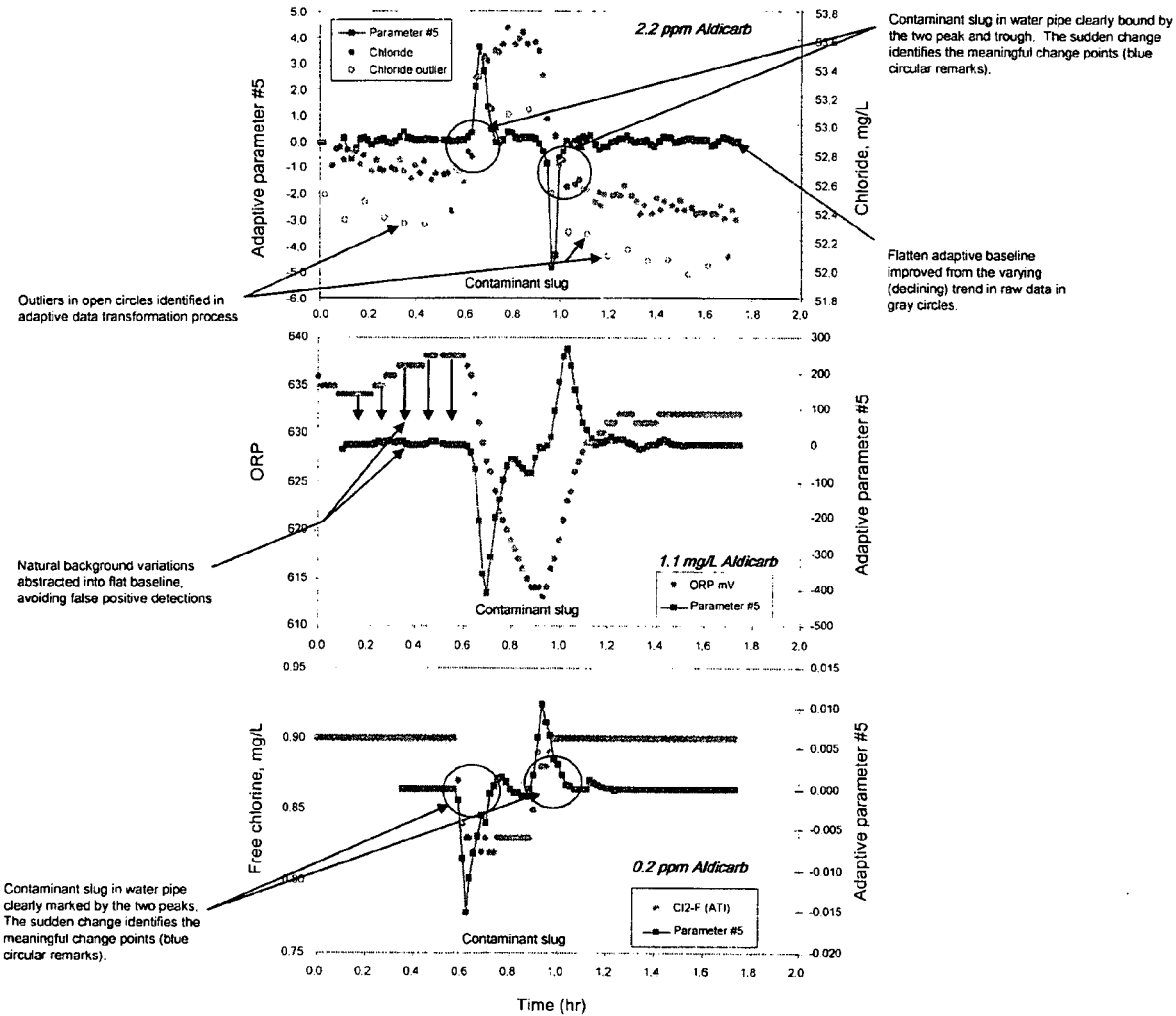

FIG. 4 contains t-series plots showing that the adaptive techniques of the said invention produce flat background baselines of free chlorine, chloride, and ORP for pesticide aldicarb experiments at 0.2, 1.1 and 2.2 mg/L concentrations. Background variations and signal drifting in ORP and chloride are eliminated through the adaptive treatment. The effect enhances contaminant signal identifications.

Figure 5:
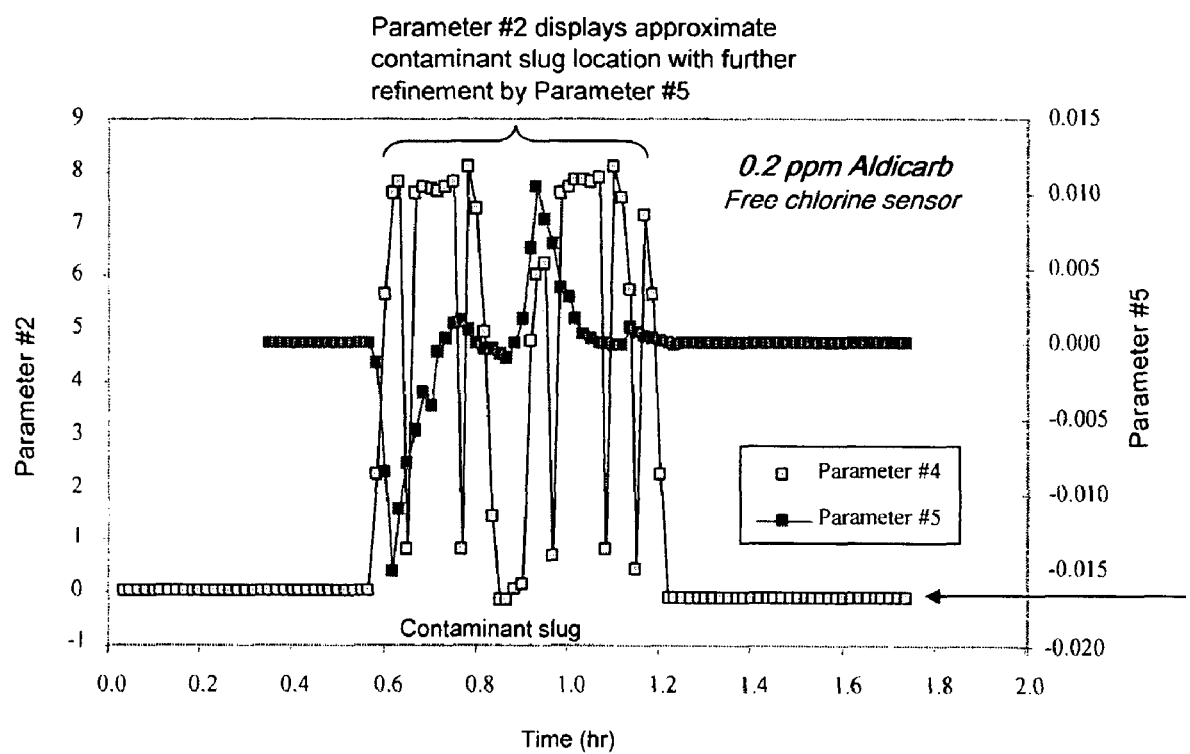

FIG. 5 shows consistent detection of anomalies and the contaminant position by both adaptive parameters #2 and #5.

Figure 6:
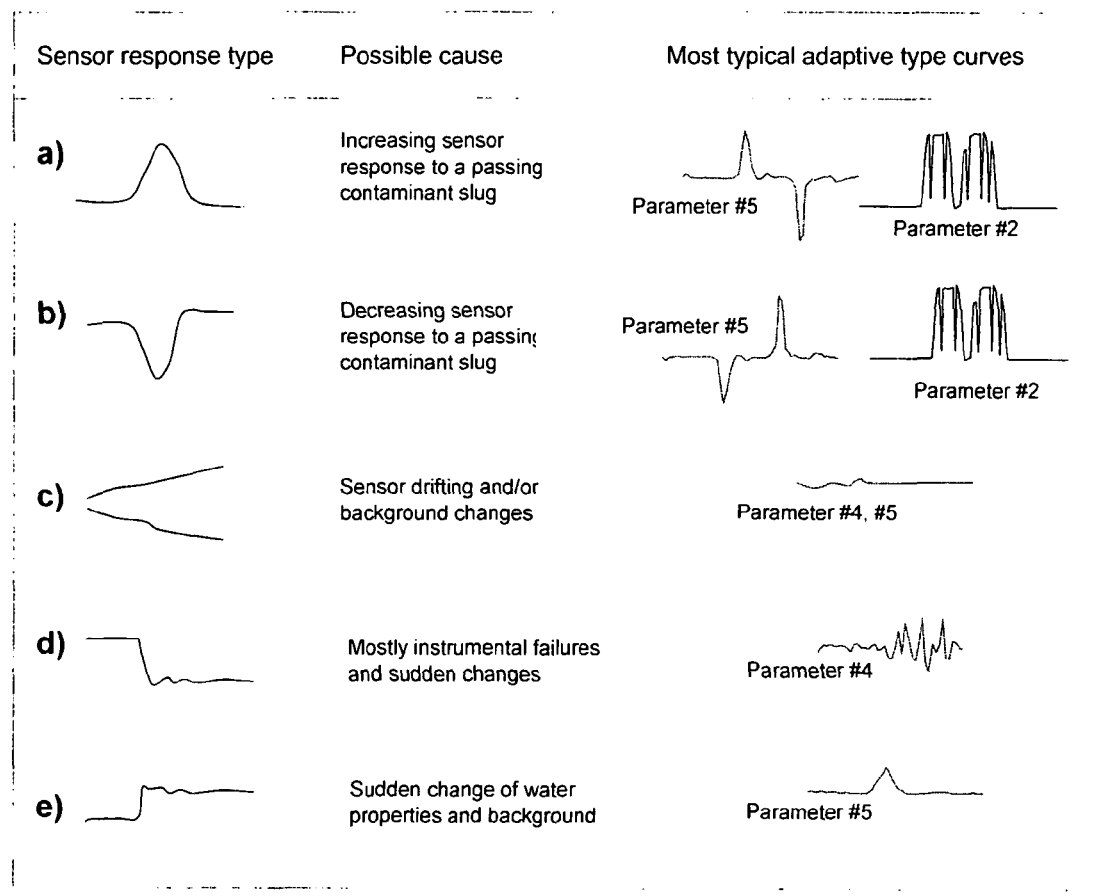

FIG. 6 shows examples of characteristic type curves using adaptive parameters for contaminant, background variations, and instrument failures. A library of characteristic adaptive type curves (partial), using five (5) Parameters to distinguish contaminant slugs from natural processes is shown. Type curves are based on time-series plots and the five parameters in adaptive detection procedures in FIG. 2. Examples were taken from adaptive analysis of the experimental results.

Figure 7:
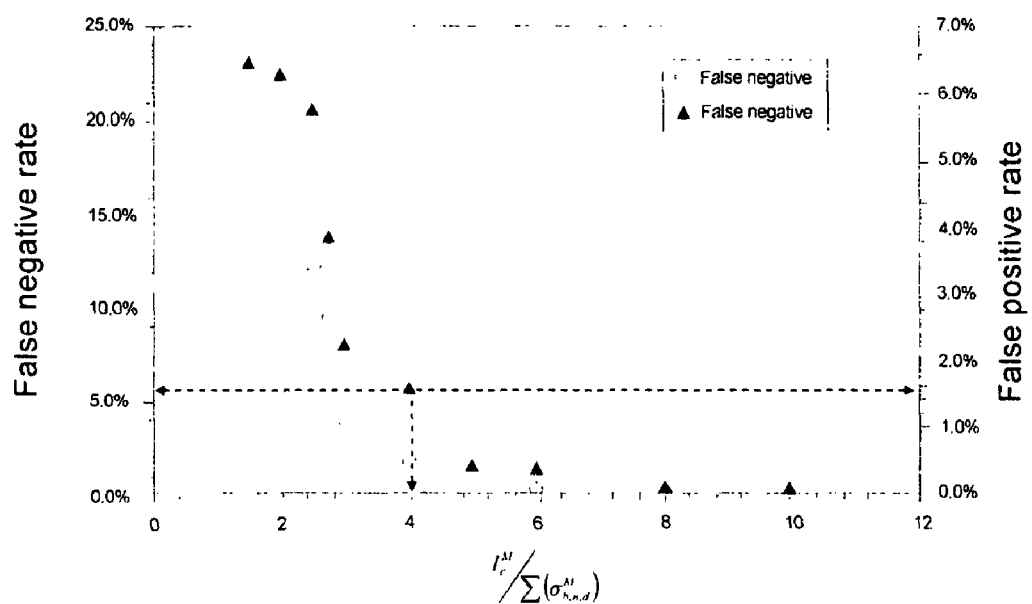

FIG. 7 shows false rates of the adaptive detection method using Monte Carlo simulations. The false rate falls below 5% when contaminant signal is 4 times higher than one standard deviation of baseline signal variations. Based on the simulation results, the method false negative rate and false positive rate can be theoretically maintained at less than 5.6% and 1.7%, respectively, for the methods of this invention.

Figure 8:
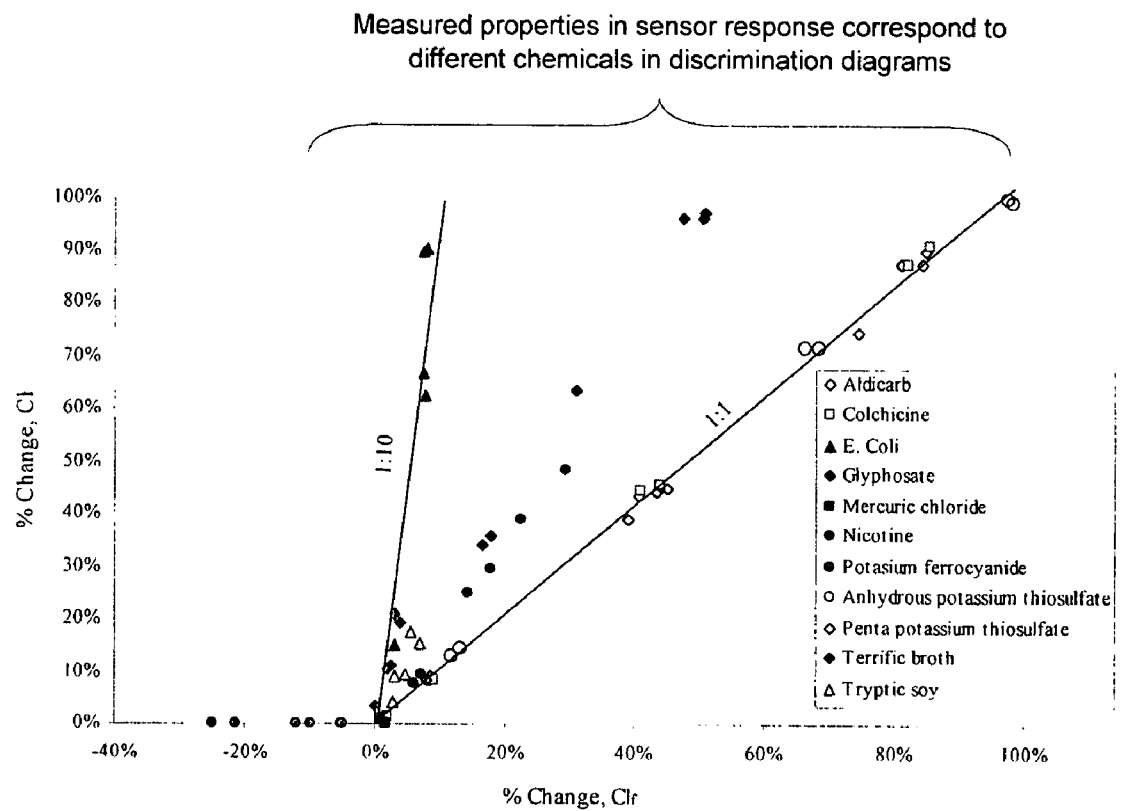

FIG. 8 shows an example of inter-parameter relationships in sensor responses of experimental data of 11 contaminants in water. The relationships are used to distinguish contaminants in Step Two of the detection procedure.

Figure 9:
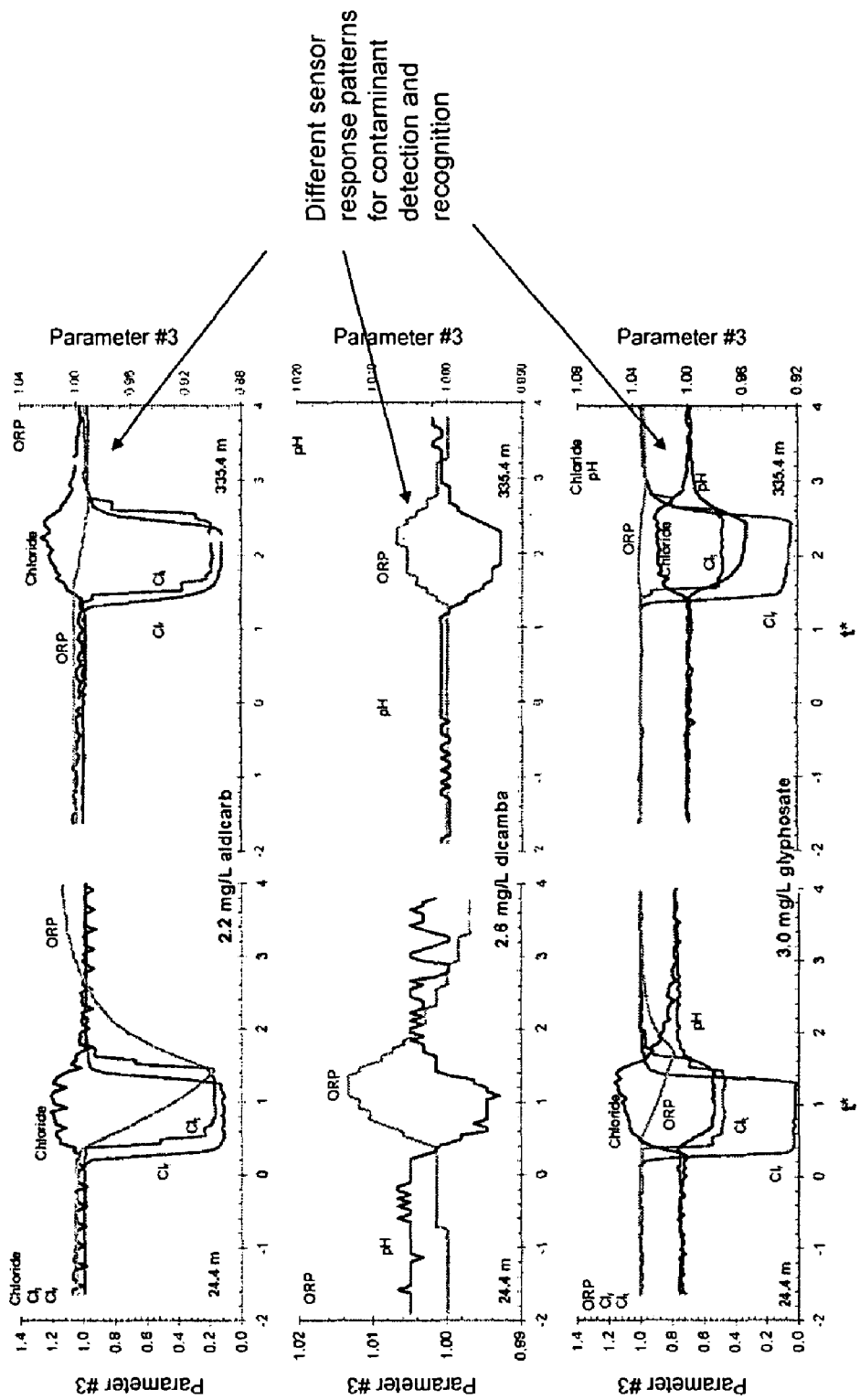

FIG. 9 illustrates examples of spatial correlations between paired sensor stations for a positive identification of contaminant slugs in Step Three. The unique patterns seen for three insecticides and herbicides are also used in Step Two of the detection process.

Figure 10:
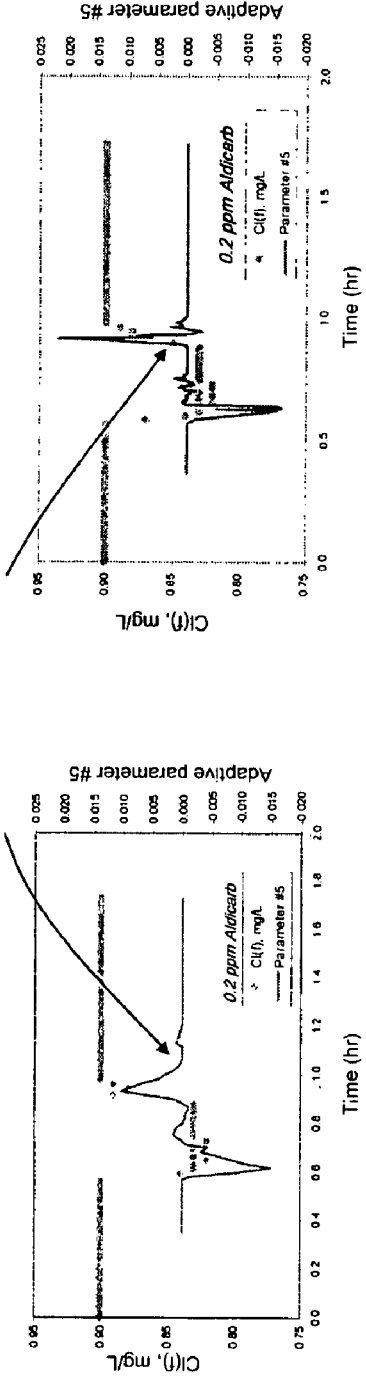
Figure 10:
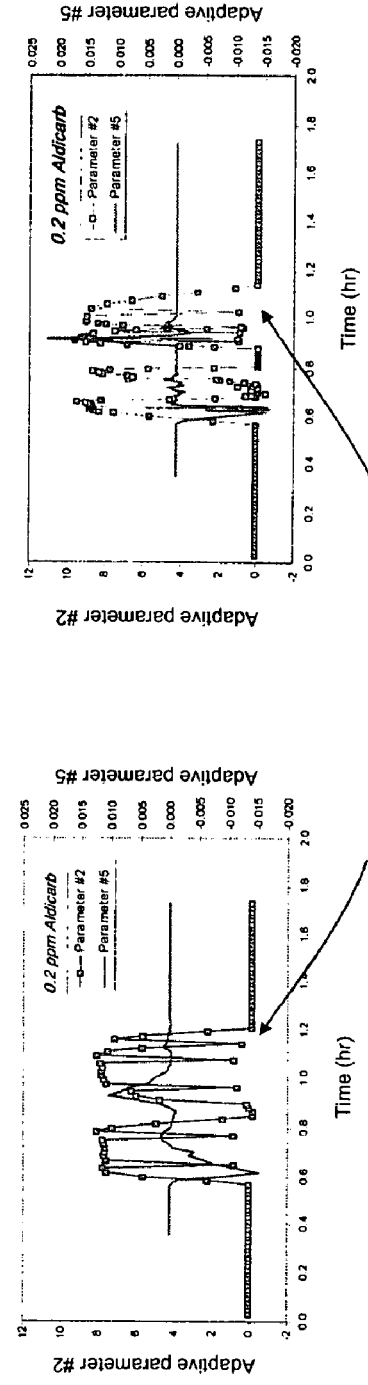

FIG. 10 shows improvements in detection through the use of an adaptive sampling schedule. The enhanced signal is aimed for detections at lower concentrations and thus for false negative detections. Example is for the 0.2 mg/L (ppm) aldicarb experimental testing.

IV. DETAILED DESCRIPTION OF THE INVENTION

Optoelectronic and other conventional water quality sensors offer a potential for real-time online detection of chemical and biological contaminants in a drinking water supply and distribution system. The nature of the application requires sensors of detection capabilities at low contaminant concentrations, for continuous data acquisition and management, and with reduced background noise and low false detection rates for a wide spectrum of contaminants. To meet these application requirements, feasibilities of software-based methods were examined and a novel technique was developed using adaptive monitoring and contaminant detection methodologies. This new monitoring and early detection framework relies on the local adaptive and network adaptive sensors in order to reduce background noise interference and enhance contaminant peak identifications. After "noise" reduction, the sensor measurements can be assembled and analyzed for temporal, spatial and inter-parameter relationships. Further detection reliability improvement is accomplished through signal interpretation in term of chemical signatures and in consideration of contaminant fate and transport in pipe flows. Based on this integrated adaptive approach, a data statistical compression technique can be used to process and reduce the sensor onboard data for background variations, which frequently represent a bulk of inflowing data stream.

The adaptive principles and methodology were examined using a pilot-scale distribution simulator at the U.S. EPA Test & Evaluation facility. Preliminary results indicate the research and development activities on adaptive monitoring may lead to the emergence of a practical drinking water online detection system.

When one employs a series of sensors in spatial relationship with and a contaminant is detected, the water located downstream may be drained until the slug containing the contaminant or other undesirable property has been removed from the distribution network. A sensor located downstream from the drain will monitor the water after draining to ensure complete removal of the water, which is not compliant with standards.

To further reduce the false detection rates and improve the anomaly detection confidence, sensor response properties and their assemblies are introduced as another layer of adaptive detection in the present invention. Data analysis using the technique is conducted after sensor data processing, which strips away and reduces signal interference (e.g., natural background variations, instrumental noise and drafting). The sanitized signal highlights the impact of contaminants on water sensor readings thereby providing lower rates of false positive and false negative detection. In the analysis, discrimination techniques are administrated to analyze the sanitized sensor responses and their characteristic assemblies or signatures. Water quality parameters measured in the two sensor stations included conductivity, turbidity, DO, ORP, pH, total and free chlorine, and chloride.

1) Detection Process Descriptions

Figure 1:
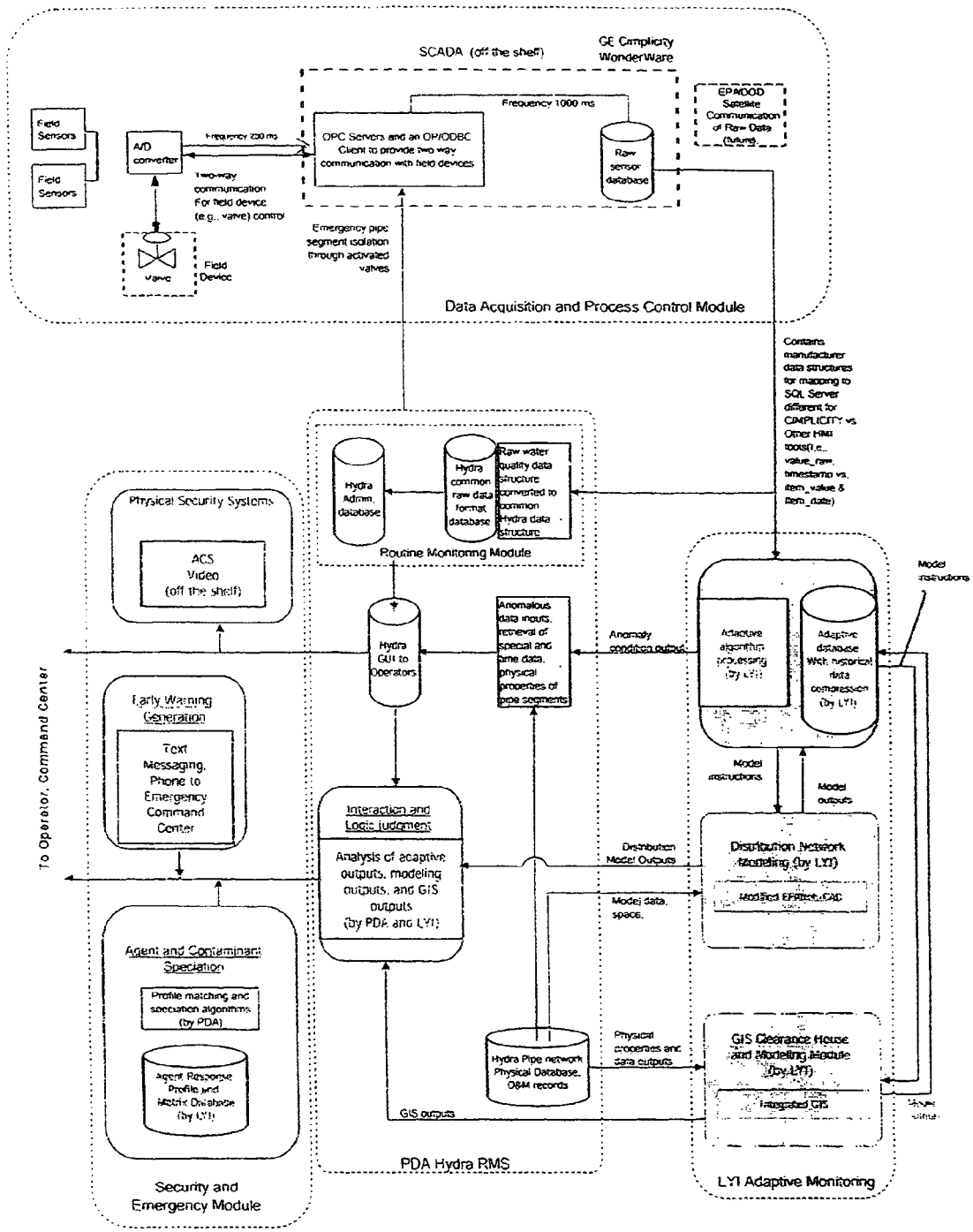
FIG. 1 shows a schematic of the detection process.

The invention employs a set of paired monitoring stations in a distribution network (See FIG. 1). Similar detection architecture has been used in computer industry on internet intrusion detection, on board naval ships in hazardous agent detection, and in environmental remediation investigations. Like the present invention, these techniques all focus on detection of small probability events among "noisy" background at an acceptable false detection rate.

An embodiment of the present invention is shown in FIG. 3 with the arrangement of paired monitoring stations. As a contaminant slug flows through LMS-A1, measurements by water quality sensors are analyzed in an adaptive detection procedure following Step 1 and Step 2 (See FIG. 2). Same detection procedure is administrated to LMS-A2. When finished, any detection is further analyzed for spatial correlation in Step 3. The detection sequence is simultaneously preceded for pair LMS-D1 and LMS-D2 at another local monitoring station (LMS). Finally network-wide spatial correlations are analyzed adaptively for all paired LMS in the drinking water distribution system.

Specifically the received sensor signals or measurements are processed in three steps at each LMS, the sequence of which can be modified according to specific monitoring conditions.

Step One—Signal Classification and Change Detections.

In the first step, sensor measurements are adaptively transformed to sensor response ratios and sanitized for gross outlier identification. The adaptive transformation follows the least-square local polynomial regression (LSLPR) techniques in a moving time window. It is aimed to classify new measurement data, detect change points and anomalies. Time window in the LSLPR analysis is kept dynamic as an art of the said invention.

Outputs from Step One include a judgment whether the incoming data pair $(I_{N,i}{}^M,t)$ is an anomaly, background baseline, or a data outlier of unknown origin. Detection principles must conform to the established contaminant transport theories in pipe flows (Biswas, et al (1993). *A model for chlorine concentration decay in drinking water distribution pipes*. Water Res., v. 27(12), 1715-1724; Rossman, (2000), *EPA-NET Version 2 users manual*, Water Resources and Water Supply Division, U.S. EPA, Cincinnati; Clark et al, (2005). *Characterizing pipe wall demand: Implications for water quality modeling*. J. Water Res Planning and Management, May/June, 208-217), and to the sensor sampling schedule changes. In the case of non-detection, the data are registered in a baseline database and background data abstraction is updated as (as mentioned in FIG. 2. Analysis for outlier and anomaly detections is then preceded in Step Two.

Step Two—Adaptive Analysis of Internal Relationships Between Multiple Water Quality Parameters and their Changes Drinking water monitoring uses multiple sensors to measure several conventional water quality parameters at a single LMS. Examples typically include total chlorine, free chlorine, chloride, dissolved oxygen (DO), pH, oxidation-reduction potential (ORP), specific conductivity, density, and turbidity. These sensors are widely available in market. Optimization of sensor bundling and assembly is well known and used in the field.

Operational principles for Step Two detection are the post-release chemistry and fate of contaminants in water flows. Drinking water in a distribution pipe network contains disinfectants such as free chlorine, an oxidant that is a principal component of household bleach. The disinfectants and other water-born chemicals react with introduced contaminants producing a suite of characteristic sensor responses. When assembled in patterns, unique patterns frequently result, which allows the responses to be used to confirm the detections and to infer contaminant classes or even specific compounds.

If inter-parameter relationships does not qualify for a contaminant detection, the transformed sensor data pair $(Y_{N,i}{}^M,t)$ is re-classified as a part of the background baseline variations. Baseline updating and data abstraction is preceded (See FIG. 2). When the detection is confirmed, a sensor sampling schedule is then modified adaptively followed by the Step Three detection.

Step Three—Spatial Correction and Detection Confirmation.

This step can be alternated with Step Two in adaptive detection sequence. It is based on transport of contaminants in water pipes. In theory, contaminants transport in a form of slug or a body of contamination that reacts, disperses, and moves along with the bulk water (Levenspiel, (1972) *Chemical reaction engineering*. John Wiley & Sons, New York). The spatial relationship of a moving contaminant slug is another independent criterion for an embodiment of the present invention.

In the invention, two paired sensor locations are configured along the same water flow path. Their distance $(S_a, S_d$ in FIG. 3) and the transformed sensor response correlations are embodiments of the present invention. Once the examination confirms the detection, it can be said with high confidence that a contaminant slug had been in the distribution system and passed through the LMS at a particular time. Then real-time early warning can be generated and communicated (FIG. 2).

If the detection is not confirmed in Step Three, the data pair is re-classified and used to update baseline in data abstraction. See FIG. 2. Furthermore, an embodiment of the present invention stipulates for a detection library that contains detection time, sensor responses and patterns for detections registered in the all adaptive steps. This information is maintained for future detection reference in data anomaly identification for causes such as contaminant intrusions, natural background variations, and instrument failures.

Upon detection of the contaminants at individual LMS, a sensor network-wide detection and analysis is invoked. This higher level of spatial relationship is used to further qualify contaminant migrations in a drinking water distribution system. A range of analytical tools can be used, including contaminant transport computer model EPANet (Rossman, 2000 supra).

Figure 2:
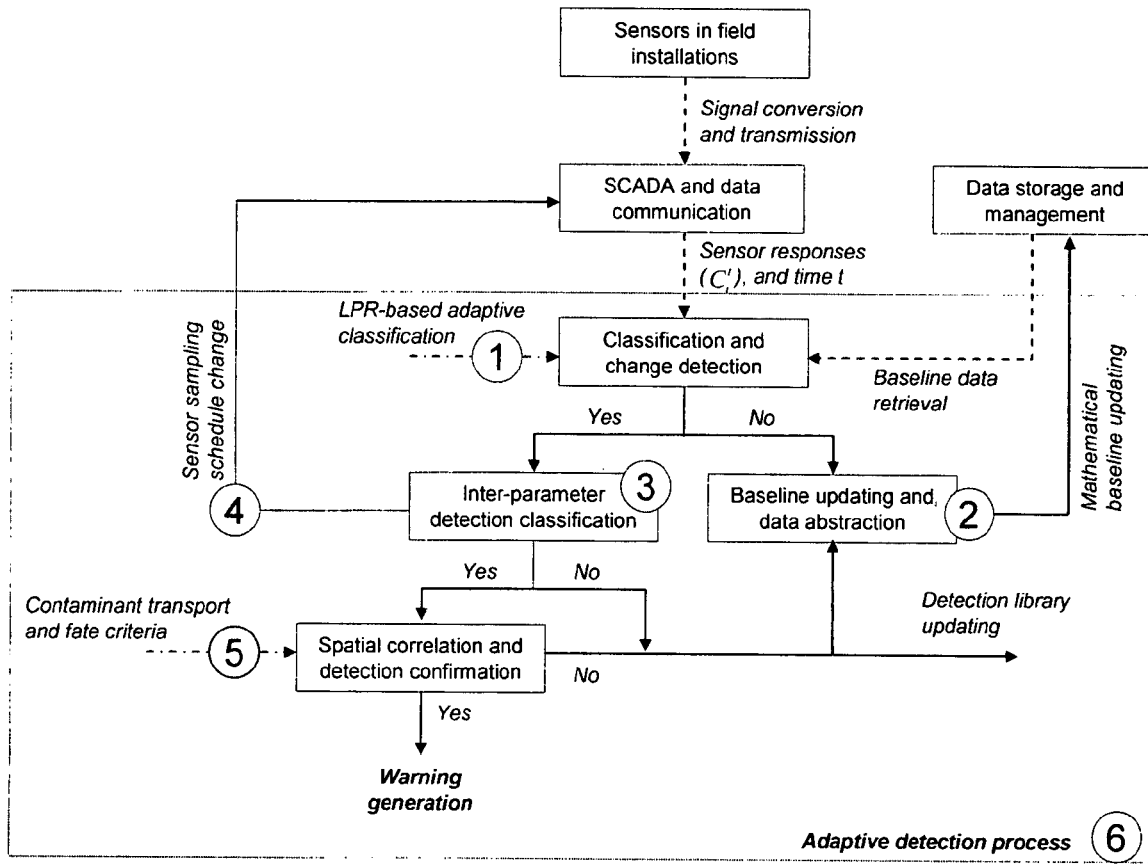
FIG. 2 is a process flow diagram of the present invention in real-time adaptive contaminant detection and early warning applications.

The first preferred embodiment highlighted as 1 in FIG. 2 is a LSLPR-based adaptive detection and classification techniques for anomaly detections. The methods and algorithms used may be of adaptive least-square local polynomial regression (LSLPR) techniques for anomaly detection in a drinking water distribution system. The computation technique employs adaptively transformed sensor response ratios in classifying major types of data anomalies. It contains iterative steps of forward and recursive LSLPR, residual analysis, comparative analysis of polynomial functions, and new data classification. Through these procedures, the technique offers several advantages including:

a) Flat baseline for enhanced anomaly detection and expanded sensor capability. Through the adaptive sensor data transformation, the water quality variations in background are corrected and transformed into a flat line. The purpose is to reduce the masking effect of background "noise" on contaminant signals. Through the transformation, sensor response ratios are generated through mathematic comparison of adaptive LSLPR expressions. Its mathematic principle stands on the sensor signal superposition and separation (Yang et al., 2006 supra) among contaminant (c), background variations (b), instrument noise (n) and drifting (d), and operational errors ($\epsilon$):

$$I_{n,t}{}^M = I_c{}^M + I_b{}^M + I_n{}^M + I_d{}^M + \epsilon \tag{1}$$

FIG. 4 shows flat baselines in the adaptive parameter #5 when experimental test data for pesticide aldicarb are adaptively transformed. Aldicarb was tested at 0.5, 1.1 and 2.2 milligrams per liter (mg/L) concentration. Robustness of the adaptive procedure can be observed from the 3 selected examples in background variations: 1) relative stable background in free chlorine; 2) small but irregular (i.e., unstable) background variations in ORP; and 3) background drifting in chloride. In all cases, the background variations are corrected and transformed into a flat baseline. Only anomalous peaks and troughs stand out indicating positions of the contaminant slug.

The aldicarb tests were administrated using a pilot-scale distribution system at the U.S. EPA Test and Evaluation (T&E) facility in Cincinnati (Haught et al., (2005) *The bench-scale minimum threshold experiment*. WQTC, Toronto, Canada; and Yang et al., (2006) *Adaptive monitoring to enhance water sensor capabilities for CBN contaminant detection in drinking water systems*, In proc. SPIE 06 Defense & Security, Orlando, Fla. The system consists of a lined cast iron pipe of 365.9 meters in length and 7.6 centimeters in diameter.

b) Change point detection for robust anomaly detections. Change point detection is a fundamental step in real-time contaminant detection. A change point refers to significant changes in sensor response variations in a t-series plot. For an embodiment of the present invention, the new sensor response is analyzed and sanitized using a forward LSLPR in a moving time window. This procedure calls for two alternative LSLPR expressions competing for data representation as guided by robust statistics. To detect and classify anomalous change points, an embodiment of the present invention uses 6 adaptive parameters defined by combinations of the LSLPR analysis results.

Adaptive parameter #5 is one example. This mathematical combination of residual and variance is robust in change point detection. As shown in FIG. 4, the contaminant slug edge and tail are clearly and univocally marked in the form of a peak-trough off flat baseline. Their positions mark change points in the sensor responses, reflecting the movement of a contaminant slug cross a sensor station.

In FIG. 5, both parameter #2 and #5 are used. Their mutual agreement confirms the contaminant slug identification. More combinations are available from other adaptive parameters, offering a toolbox for the said invention in detection confirmation. The response combinations define a sensor response matrix or patterns, forming a library of characteristic type curves for anomalies of different origins (FIG. 6).

c) Low false identification rate. The LSLPR techniques in Step One alone can provide detection at a false rate below 5% when sensor response to contaminant (i.e., concentration) is greater than 4 times of the background variances. This target performance is based on the results of 500 Monte Carlo simulations at each of the simulated contaminant concentrations (FIG. 7).

The 5% target false detection rate is further reduced when initial detection is verified in subsequent two steps (FIG. 2). As described latter, the Step Two and Step Three identification is based on techniques of chemical relationships and detection spatial correlations, respectively. They are independent of sensor response properties used in Step One detection, making further reduction in false detection rate.

In addition to a Monte Carlo computer simulation, the claimed performance in low false rate was demonstrated in experiments using a pilot-scale distribution system at the U.S. EPA Test and Evaluation facility in Cincinnati. The detection for all 15 tested compounds was 100% with no false detections:

Aldicarb, 0.2-2.2 mg/L
Dicamba, 0.8-2.6 mg/L
Glyphosate, 0.4-3.0 mg/L
Colchicine, 0.4-3.6 mg/L
Lead nitrate, 0.6-1.4 mg/L
Mercury chloride, 0.4-2.2 mg/L
Nicotine, 0.4-3.8 mg/L
Potassium ferrocyanide, 0.6-3.2 mg/L
Anhydrous potassium thiosulfate, 0.2-2.6 mg/L
Penta potassium thiosulfate, 0.2-2.4 mg/L
Sucrose, 0.6-3.6 mg/L
*E. Coli,* 0.01-0.14 1000 cfu/L
Nutrient broth, 0.12-0.95 mg/L
Terrific broth, 0.12-0.95 mg/L
Tryptic soy, 0.12-0.95 mg/L A second preferred embodiment of the present invention is in the field of techniques in background data abstraction and baseline updating. Baseline updating is a component of the Step Two in the adaptive detection process (FIG. 1). This technique designed for drinking water distribution network aims for better operational efficiency through data volume reduction in storage and management.

In this technique, two alternative polynomial expressions $\hat{\beta}F(t)$ compete to represent sensor response data in a moving time window. The used forward and recursive computations are guided by the regression performance. Through the procedure, transformed background data $[Y_{N,i}^M, t]_{t=1,2,3...n}$ are abstracted and represented by a set of statistical variables $\{t_1, t_n, \hat{\beta}, R^2\}$. Namely, $$[Y_{N,i}^M, t]_{t=1,2,3...n} = \hat{\beta}F(t) + \zeta \qquad (2)$$

Variable $F(t)$ is a polynomial expression; $\hat{\beta}$ is a 1×n matrix of coefficients; and $\zeta$ is a matrix of residuals. The adaptive detection process can use the data $\{t_1, t_n, \hat{\beta}, R^2\}$ instead of the raw sensor data for the time period. This simplification reduced working load in computation and data management. The advantage is apparent when the said invention is applied to a large distribution system when a substantial number of monitoring stations exist in the network.

A third preferred embodiments of the present invention are techniques of inter-parameter correlations for positive contaminant slug identification and contaminant classification. This includes detection verification and contaminant classification using inter-parameter correlations. The detection procedure is located in Step Two and follows the initial anomaly and change point detection on t-series relationships in Step One (FIG. 2).

This embodiment of the invention stipulates that when contaminants are introduced to water, they either react or displace and mix with natural drinking water in the pipe. As a result, the introduction leads to change certain water quality parameters. The adaptive methods amplify the changes, and 'package' them in a set of combinations that are characteristic of the contaminant properties. This procedure furthers the anomaly detection and allows for contamination identification. Examples are shown in FIGS. 8 and 9.

In FIG. 9, the tested insecticide and herbicides have characteristic response patterns at each sensor station. When assembled, they form a different type of inter-parameter relationship for contaminant classification. In FIG. 8, tested contaminants differ from each other in the relationships between total chlorine and free chlorine depletion. The depletion (by removal or reaction with contaminants) is determined in the adaptive technique. For example, bacteria *E. Coli* is located at 1:10 line whereas pesticide aldicarb is plotted along the 1:1 ratio.

When reacting with disinfectants and other chemical species in drinking water, contaminants of different class exhibit unique patterns in sensor responses. Haught et al, supra, reported differential sensor responses in multiple water quality parameters to contaminants in the bench-scale experiments. In the experiments, diacamba, a widely used herbicide ingredient shows little reactivity with chlorine, possibly because of its stable benzoic acid structure whereas glyphosate, the principle active compound in commercial herbicide Roundup™, reacts readily with chlorine of concentrations in drinking water. This observation indicates there is a potential that responses from the multi-parameter sensor assembly can form a number of combinations serving as the discriminating chemical signatures, based on which one could identify contaminants or their chemical classes. A prerequisite for this capability is the adaptive sanitization of sensor responses that suppresses background interference and enhances contaminant signals.

The degree of chlorine depletion appears proportional to aldicarb concentrations in FIG. 9. Using the data sanitization technique, the depletion can be precisely quantified. The results indicate that using two sensor stations have similar degrees of chlorine depletion and the primary factor controlling sensor response is the contaminant concentrations.

It is further observed that relative to the hydraulic retention time, the chlorine depletion is delayed to pass through the sensor stations. Such a delay ($\Delta t^*$) increased slightly with the flow distance, while the width of chlorine depletion remains a constant approximately equal to that of the contaminant slug (FIG. 9).

A fourth preferred embodiments of the present invention are techniques in adaptive sampling schedule changes for better detection. A sampling schedule refers to types of sensor data acquired and the frequency at which the data are acquired. This technique considers the facts that a contaminant slug has a limited volume and the detecting its front and tail can be difficult in real-time monitoring. Logistics of a covert operation would restrict the volume of contaminants used. Similar restriction applies to contamination in natural intrusions to a distribution network. For example, negative pressure from breaks of a water pipe only lasts for several to tens of seconds each time (AWWA, 2004 supra). Only a limited volume of foreign contaminants could be siphoned into the pipe.

Because of the small potential contaminant volume, sensor measurements using regular sampling schedule can "miss" the front and tails of a moving contaminant slug. This can lead to incomplete contaminant characterization, and often generate insufficient number of measurements to make a firm statistical cluster distinction. In such cases, a false negative detection occurs.

To overcome the detection difficulty, this embodiment of the present invention changes the monitoring schedule (usually to a more frequent sensing) when anomaly or change point is detected in Step One and verified in Step Two (FIG. 2). In one variation, the adaptive sampling schedule change follows the rules below:

When three consecutive anomalous data points are identified, the monitoring schedule is changed to a higher sampling frequency or smaller sampling time interval. The change magnitude is guided by the variance between the new anomalous data and the background data of the adaptive time window.

Following an intensified sampling period, the schedule is returned to normal when three consecutive "normal" background values are identified.

This technique can significantly enhance detection capability for contaminant slugs of small volumes. The present invention can overcome this difficulty by using higher sampling frequency. At the same time, the adaptive sampling schedule further improves the contaminant detection. This is accomplished by enhancing the detection signals and through better depictions of the raising limb and failing tail of a contaminant slug. Nearby sensors in the same LMS or sensors in a nearby LMS may also change their sampling schedule in preparation for the approaching slug and for finer determination of the change point boundaries of the contaminant slug.

FIG. 10 shows such an example for aldicarb at 0.2 mg/L concentration. Detection results are displayed side by side for normal and adaptive schedules.

A fifth preferred embodiments of the present invention are techniques of networked and paired sensors to confirm contaminant slug detection. This embodiment relates to the technique and its variations using spatial correlations between two or more spaced sensors within a single LMS. This technique is used in Step Three of the adaptive detection process (FIG. 2). In this step, the contaminant slug identification is verified through spatial relationships for multiple measured water quality parameters. The correlation must conform to contaminant transport in pipe flows as described in Levespiel (1972) supra and Rossman (2000) supra.

An example of spatial correlations is shown in FIG. 9 for experiment testing at the U.S. EPA Test and Evaluation facility in Cincinnati. The changes in all measured water quality parameters are highly correlated between the two spaced monitoring stations (Yang et al., 2006 supra). Based on these qualitative and quantitative relationships, it can be firmly concluded that the contaminant slugs were detected at the sensor stations. Specific time passing the stations can be defined and reported (FIG. 2).

A sixth preferred embodiment of the present invention is a three step adaptive process for real-time contaminant detection. In this process, all adaptive detection techniques work together and provide real-time contaminant detection at a low false rate. It has advantages including:

Through adaptive monitoring, the technique adapts to natural variations and distinguishes them from contaminant anomalies. Therefore, it does not require data training of a lengthy time, for example, a year or more to some existing anomaly detection algorithms. This advantage allows the technique to be deployed on-demand at desired locations.

The technique is based on a three-step process using independent variables (i.e., t-series, inter-parameters, and spatial correlations) for anomaly detection. It employs the techniques of robust statistics, and adaptive analysis of temporal, spatial and chemical relations. This contrasts to only statistical criteria in other anomaly detection methods and algorithms. Consequently the said invention has low false identification rates as the clear advantage. Target false rate is below 5%. In limited experiments for 15 contaminants, no false detection occurred for the test conditions.

Quantitative relationships used in discrimination diagrams make it possible to infer contaminant types or classes, an improvement over existing outlier and anomaly detection methods.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

What is claimed is:

1. A method for detecting an anomaly in a water distribution system comprising, flowing water by a sensor to measure a component of the water, determining a background baseline for the component,
determining a background variation for the component,
correcting and transforming the data from the sensor into a flat line for a new baseline, and
determining when an anomaly occurs by measuring an amount of the component of the water, which deviates more than the background variation for the component from the new baseline.

2. The method according to claim 1 wherein the component is a chemical.

3. The method according to claim 1 wherein the component is dissolved in the water.

4. The method according to claim 1 further comprising a plurality of different types of sensors for determining different components of the water.

5. The method of claim 4 wherein the new baseline is formed individually for each of a plurality of different components of the water.

6. The method according to claim 5 wherein the components are chemicals.

7. The method according to claim 5 wherein the components are dissolved in the water.

8. The method according to claim 4 wherein the ratio between the different components in the water is determined.

9. The method of claim 8 further comprising determining a background baseline for the ratio,
determining a background variation for the ratio,
correcting and transforming the data from the ratio into a flat line for a new baseline, and
determining when an anomaly occurs by determining when the ratio deviates more than the background variation for the ratio from the new baseline.

* * * * *